United States Patent
Matay

[11] 3,981,184
[45] Sept. 21, 1976

[54] ULTRASONIC DIAGNOSTIC INSPECTION SYSTEMS

[75] Inventor: Istvan M. Matay, North Royalton, Ohio

[73] Assignee: TRW Inc., Cleveland, Ohio

[22] Filed: May 7, 1975

[21] Appl. No.: 575,572

[52] U.S. Cl. .............................................. 73/67.8 S
[51] Int. Cl.² ......................................... G01N 29/04
[58] Field of Search............ 73/67.8 R, 67.8 S, 67.9

[56] References Cited
UNITED STATES PATENTS

| | | | |
|---|---|---|---|
| 3,021,706 | 2/1962 | Cook et al. .......................... | 73/67.8 S |
| 3,023,611 | 3/1962 | Howry ................................ | 73/67.8 S |
| 3,534,590 | 10/1970 | Kent et al. ........................ | 73/67.8 S X |
| 3,575,042 | 4/1971 | Lovelace ............................ | 73/67.8 S |
| 3,856,985 | 12/1974 | Yokoi................................. | 73/67.8 S X |

OTHER PUBLICATIONS

M. Onoe, et al., Application of Graphic Display to Ultrasonic Testing, Conference: Proceedings of the Society of Photo-Optical Instrumentation Engineers Seminar etc., Los Angeles, Calif., Feb. 1972.

Primary Examiner—Richard C. Queisser
Assistant Examiner—John P. Beauchamp
Attorney, Agent, or Firm—Hill, Gross, Simpson, Van Santen, Steadman, Chiara & Simpson

[57] ABSTRACT

An automatic ultrasonic inspection system for automatically testing billets by the pulse reflection type of inspection and further utilizing an ultrasonic transducer for thru-transmission of energy for automatic distance-amplitude correction and including indexing means having an angular scan encoder and an axial scan encoder such that reflections obtained indicative of defects are accurately correlated with their three dimensional positions in the billets. A defect gate receives the reflections through the billet and if a defect meets a preset criteria such defect information is displayed and passed to a computer wherein the position of the defect is stored. The computer can provide various outputs such as alphanumeric-graphic display or printed outputs.

8 Claims, 8 Drawing Figures

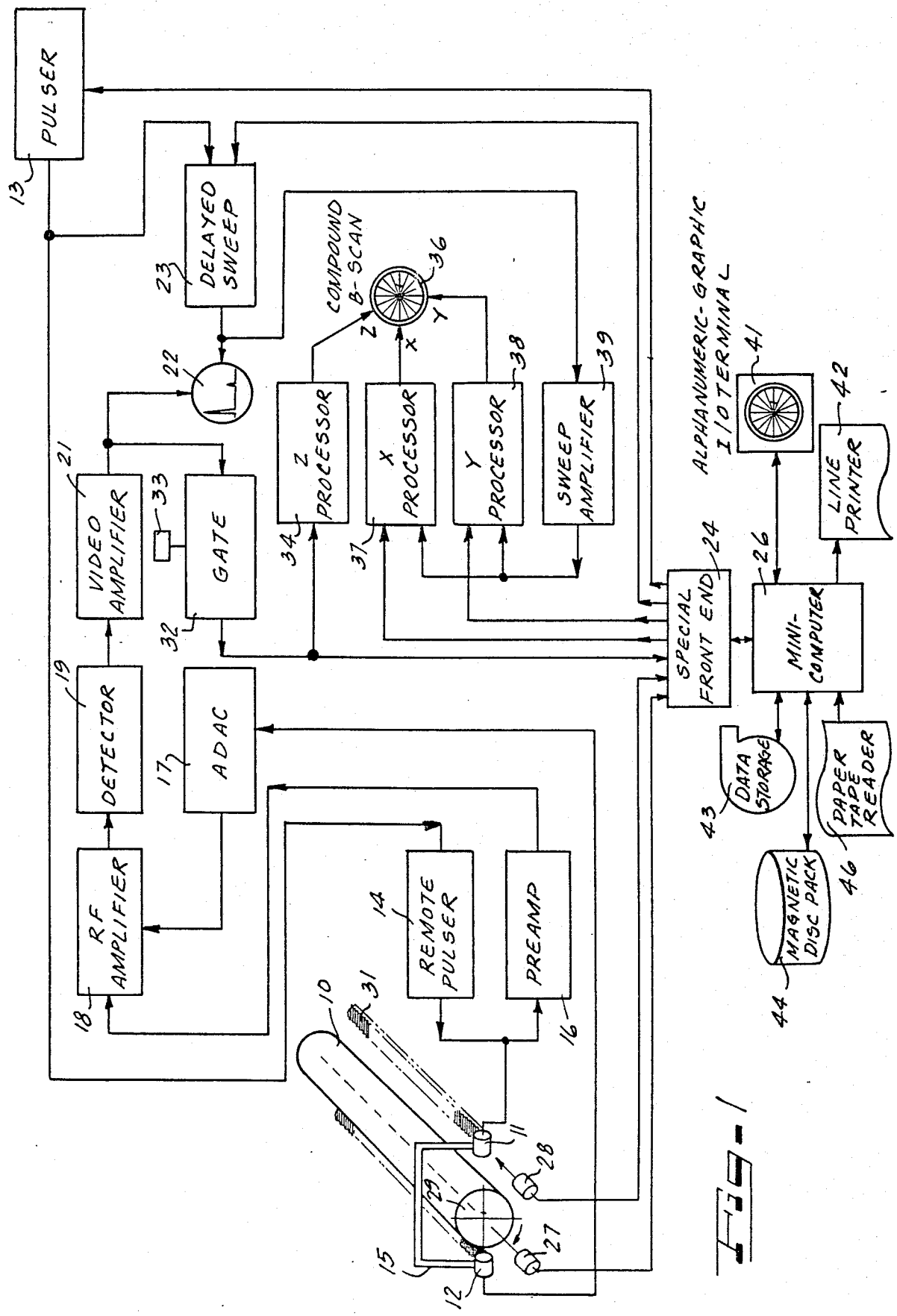

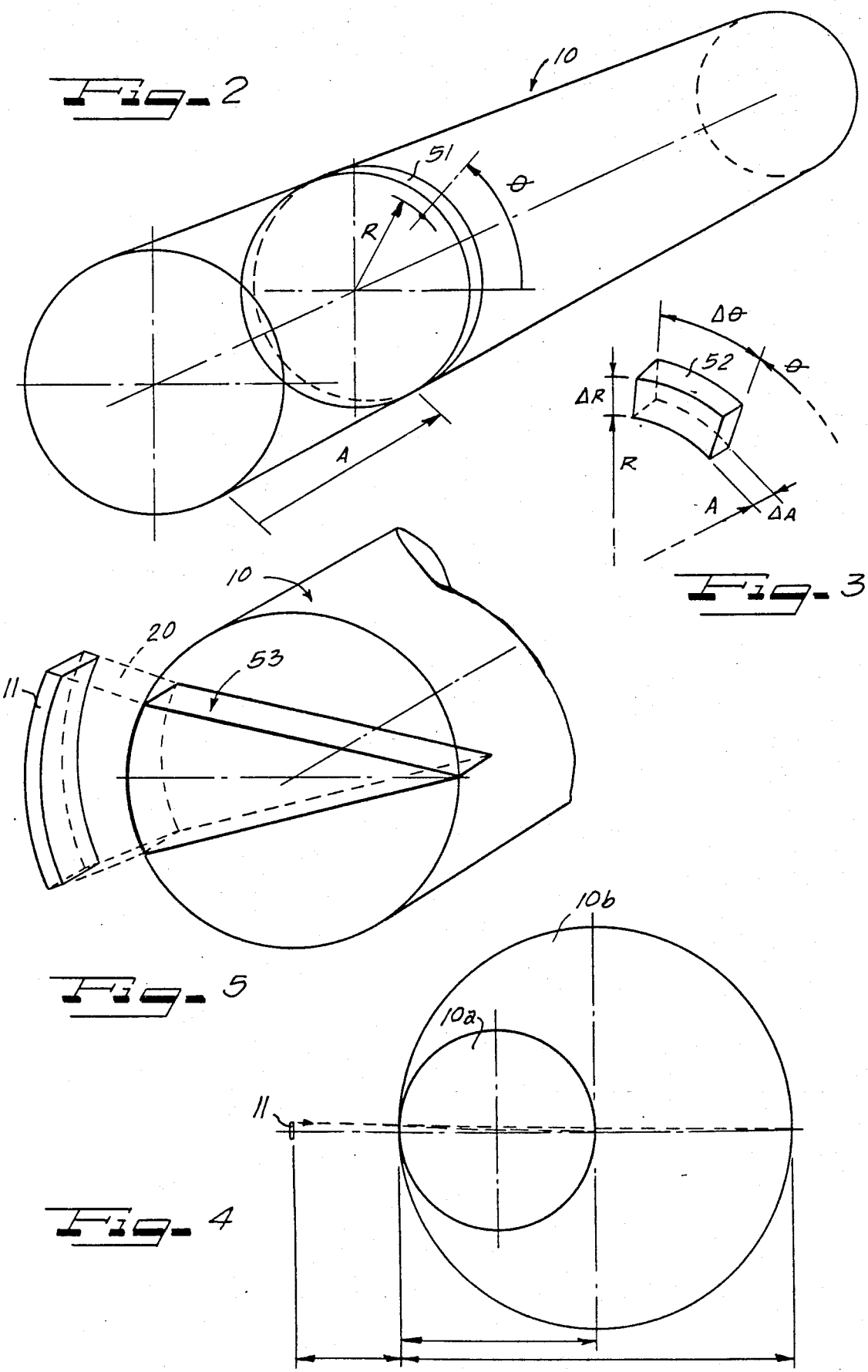

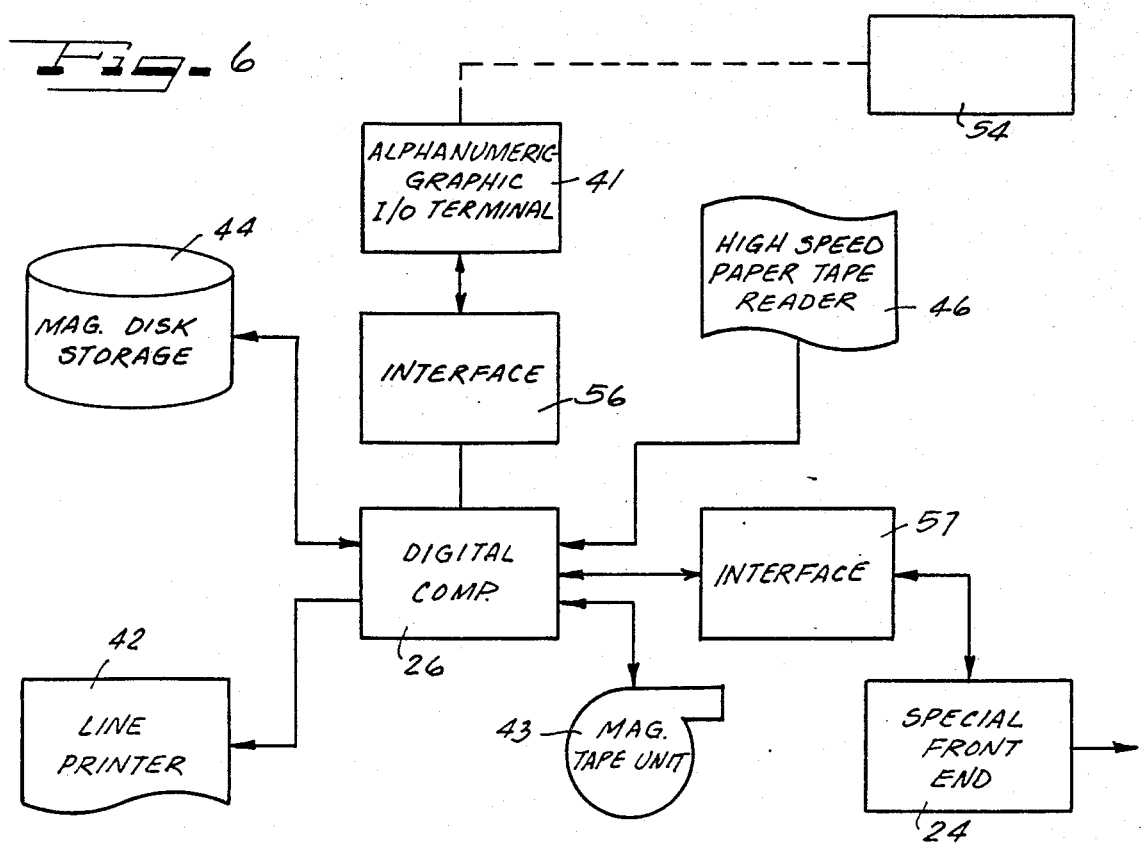
Fig-6
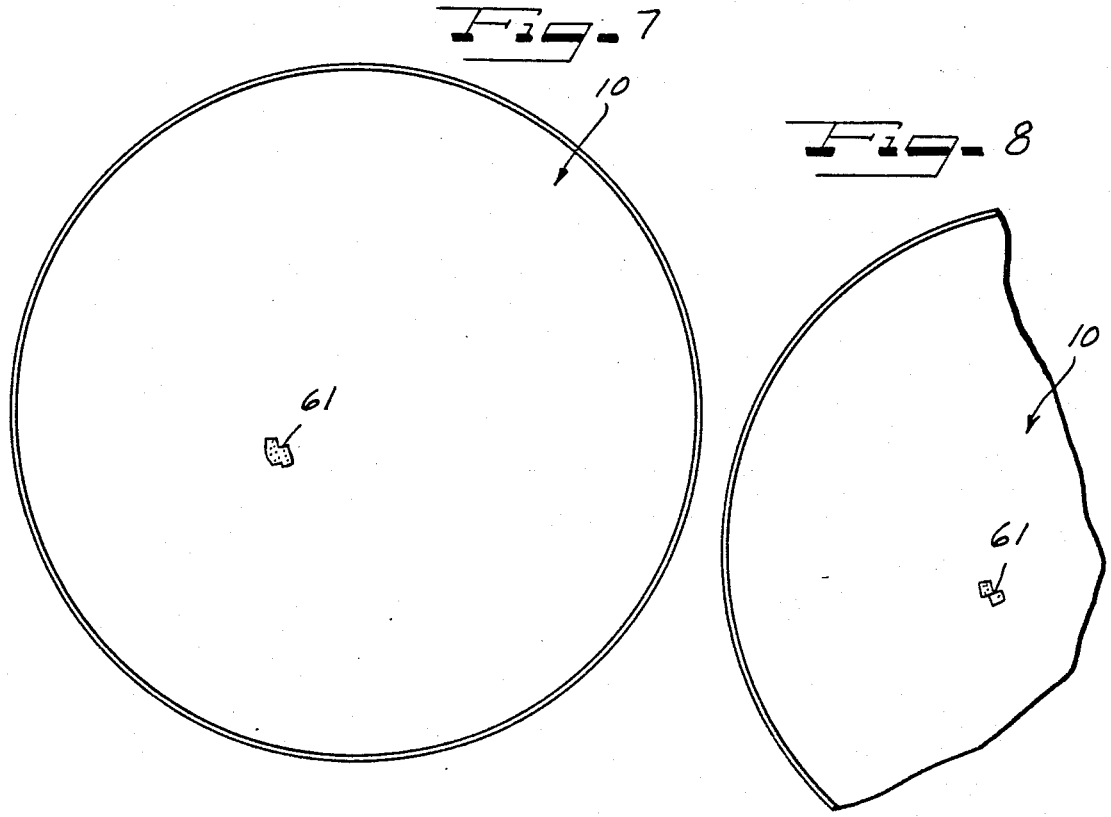
Fig-7
Fig-8

3,981,184

ULTRASONIC DIAGNOSTIC INSPECTION SYSTEMS

GOVERNMENT CONTRACT

The invention herein described was made in the course of or under a contract or subcontract thereunder with the United States Air Force.

CROSS-REFERENCES TO RELATED APPLICATIONS

This application is related to my co-pending application entitled "Ultrasonic Inspection Method of Pulse Reflection Defect Detection Using a Thru-Transmission Automatic Distance-Amplitude Compensation", Ser. No. 575,460 filed May 7, 1975.

BACKGROUND OF THE INVENTION

1. Field of the Invention

This invention relates in general to ultrasonic non-destructive testing and in particular to a new and novel system.

2. Description of the Prior Art

Ultrasonic non-destructive test equipment has been used for testing specimens and my prior U.S. Pat. No. 3,690,153. Sept. 12, 1972, discloses an ultrasonic distance amplitude correction system. Prior ultrasonic non-destructive inspection systems utilize electronic instrumentation and transducers in which a human operator is required to manipulate the electronic instrumentation and transducers and to interpret the output test results obtained. Thus, the decision as to whether to accept or reject a particular test specimen, is influenced by the particular human operator who is operating the system.

SUMMARY OF THE INVENTION

The present invention comprises a novel ultrasonic diagnostic inspection system which eliminates the variability of a particular human operator and improves the diagnostic capabilities beyond that possible with human operators. Test specimens such as cylindrical billet are subjected to testing by providing an ultrasonic transducer of the pulse reflection type which ultrasonically sweeps the billet radially while mechanically scanning the billet both angularly and axially and indexing means for locating and identifying the angular and axial position of the billet are provided. A thru-transmission transducer is also provided for automatic distance-amplitude correction and the output reflections are passed to an A-scan display wherein any defects are presented and are also provided to a defect gate which has a threshold of predetermined level and defect reflections passing such gate are displayed on a compound B-scan comprising a modified PPI display and are further stored in a computer storage device for further recall. The invention also provides scanning a particular volume increment a number of times such that a serious defect is recognized if the defect gate passes reflections a predetermined percentage of the transmitted signals.

The entire profile of the volume of the billet is available in the storage of the computer and can be provided as line printer outputs, supplied to an alphanumeric-graphic display, stored for future use, or supplied to remote locations for various purposes.

Other objects, features, and advantages of the invention will be readily apparent from the following description of certain preferred embodiments thereof taken in conjunction with the accompanying drawings, although variations and modifications may be effected without departing from the spirit and scope of the novel concepts of the disclosure, and in which:

BRIEF DESCRIPTION OF THE DRAWINGS

FIG. 1 is a block diagram of the ultrasonic diagnostic inspection system.

FIG. 2 is a perspective view illustrating the billet-defect geometry.

FIG. 3 illustrates the unit cell geometry.

FIG. 4 illustrates the acoustic examination of cylindrical billets.

FIG. 5 illustrates a pie-cut shaped cylindrical sector billet acoustic illumination pattern.

FIG. 6 is a block diagram of the data processing system.

FIG. 7 is a display of a defect in a billet, and,

FIG. 8 is a display of a defect in a billet at a different position from that illustrated in FIG. 7.

DESCRIPTION OF THE PREFERRED EMBODIMENTS

FIG. 1 illustrates the novel ultrasonic diagnostic inspection system of the invention and discloses a cylindrical billet 10 which has a first end 29. An ultrasonic transducer 11 for pulse reflection is mounted so as to transmit and receive ultrasonic energy radially into the billet 10 so as to scan all of the billet by moving around the billet or alternatively by having the billet rotate and further the transducer 11 is adapted to move axially to different positions along the billet 10 so that each volume of the billet can be scanned. Although the transducer 11 as shown in FIG. 1 moves on a carrier 31, it is to be realized that the billet 10 may be moved relative to the transducer 11 if desired. A thru-transmission transducer 12 is attached by a bracket 15 to the transducer 11 and receives energy from the transducer 11 which is passed through the billet on the opposite side of the billet.

An angular scan digital encoder 27 is mounted and indexed with the billet 10 so that it produces an output indicative of the angular position of the billet 10. An axial scan digital encoder 28 is mounted relative to the transducer 11 so as to produce an output indicative of the axial position of the transducer 11 relative to the billet 10. The output of the encoders 27 and 28 are supplied to a mini computer 26 such as a Motorola type M6800 through a front end interface unit 24 such as a peripheral interface adapter for Motorola type M6800 and the angular position theta and the axial position A are provided and stored in the memory of the computer 26. The pulser 13 receives a clock signal from the mini computer 26 through the special front end interface 24 and periodically pulses the transducer 11 and also supplies an input to a delayed sweep generator 23. The pulser 13 supplies the input to the transducer 11 through the remote pulser 14. A pre-amp 16 receives pulse echoes from the transducer 11 and supplies an output to an RF amplifier 18 which has a variable gain controlled by an automatic distance amplitude controller 17 which receives an output from the thru-transducer 12. The automatic distance amplitude controller 17 may be of the type disclosed in my co-pending application "Ultrasonic Inspection Method of Pulse Reflection Defect Detection Using a Thru-Transmission Automatic Distance-Amplitude Compensation". The output of the automatic distance amplitude controller 17 controls the gain of the RF amplifier 18 so as to correct for attenuation in the billet as well as for the distance travelled of the received energy. A detector 19 receives the output of the RF amplifier 18 and supplies it to a video amplifier 21 and it is displayed on a A-scan display 22 which also receives an input from the delayed sweep generator 23. Any defects in the billet 10 will be displayed on the display unit 22. An adjustable threshold defect gate 32 has a control 33 for setting its threshold level and receives the output of the video amplifier 21 and supplies it to a Z processor 34 which is connected to a compound B-scan indicator 36 which may be of the modified PPI type. The output of the gate 32 is also supplied to the computer 26 through the interface 24. The computer 26 supplies signals proportional to sine theta and cosine theta to an x-processor and y-processor, respectively, which supply inputs to the indicator 36. Sweep amplifier 39 supplies inputs to the processors 37 and 38 and receives an input from unit 23.

The computer 26 is connected to an alphanumerical-graphic terminal 41 for displaying the profile of the billet 10 such as shown in FIGS. 7 and 8, and is also connected to a line printer 42 for providing printed information for the billet 10. Data storage 43, a magnetic disc pack 44 and a paper tape reader 46 are also connected to the computer 26. The disc back 44 is capable of receiving information from the mini computer 26 and magnetically storing it where it can be recalled for furnishing back to the mini computer as desired. The paper tape reader 46 is capable of reading punched paper tapes upon which testing data has been recorded and supplying it to the mini computer.

The apparatus illustrated in FIG. 1 can be utilized for inspecting materials having large dimensions and high attenuation such as titanium billets and operates as follows. If the titanium billet is considered as a simple cylindrical shaped object, it can be tested and analyzed as a three-dimensional polar-rectangular coordinate system as shown in FIG. 2. The billet is inspected by a longitudinal wave injected into the material travelling in the radial direction defined by the radial coordinate (R) from the outside surface towards the center of the billet. Defects in the material cause reflections which are received by the transducer 11 and processed by the apparatus to indicate the defect. The transducer 11 is rotated or alternatively the billet is rotated so that a different segment is swept in a second time interval and this is continued until the entire disc 51 of the billet slice has been scanned. Each sweep is defined by an angular coordinate theta and the entire disc 51 is scanned resulting in the inspection of a billet crosssection slice 51 illustrated in FIG. 2. The entire billet is then inspected by repeatedly moving the transducers 11 and 12 so that successive slices are tested which comprise moving along the billet axial coordinate A illustrated in FIG. 2.

With the assignment of unit dimensions to the coordinate system comprising the coordinates R, Theta and A a specification of a unit cell geometry was established illustrated in FIG. 3. This unit cell volume 52 is designated "Sector-of-rectangular torus".

Acoustic billet illumination patterns illustrated in FIGS. 4 and 5 were designed to fulfill the requirements of the polar-rectangular billet inspection coordinate system and FIG. 4, for example, shows a billet of titanium for example, having a first diameter $10_a$ and a larger billet having a second diameter and designated $10_b$. FIG. 5 illustrates a sector-of-a-tube shaped transducer 11 for passing ultrasonic energy through a water coupling 20 into the billet 10 in a pie-cut sector of the cylinder of the titanium billet 10. The pie shaped sector is designated by 53. FIG. 5 is drawn out of proportion, in order to illustrate the acoustic illumination concept.

The invention uses digital encoder devices so as to monitor real-time billet angular and axial position locations for inspection as shown in FIG. 1 so that the billet can be monitored as the test is conducted. Also, the test results can be stored in the memory of the computer for recall at a later time.

The computer is programmed to direct inspection, to collect the inspection results, to diagnose said results, and to provide an acceptance-rejection decision and to maintain a permanent inspection data file.

The system operation may be in the following four modes; calibrate, manual, automatic and off-line. The inspection data contains (1) the defect radial location information, R (provided by the pulse-reflection mode acquired echo) and the corresponding billet angular position theta and the axial position A location of the defect. These coordinates are provided by the digital billet position monitoring encoders 27 and 28. The inspection data for each billet cross-sectional slice is transferred in real-time to the data processing sub-system for defect data analysis and permanent storage. The system is provided with three displays (1) an A-scan display 22 to produce a real-time view of the time domain response of the billet radial path under inspection; (2) a compound B-scan (PPI) display to produce a real-time view of the time domain response of the billet slice cross-section under inspection, and (3) a computer alphanumeric-graphic terminal peripheral using English conversational language to communicate between the operator and the testing system. The graphic terminal can also provide a billet cross-sectional view for all of the defective unit cells and/or another view showing only those unit cells which meet or exceed the programmed acceptance/rejection criteria based on the three-dimensional unit cell groupings. These displays and diagnoses cannot only be obtained in real-time but in a retrieved mode and repeated for various accept-reject criteria.

In order to eliminate the subjectiveness of a human operator and to improve the diagnostic capabilities beyond human capacity, the data processing system was developed and incorporated into the testing system. The data processing system accepts the information of each ultrasonic sweep of a billet radius. This data under the control of the computer 26 is summed over repetitive sweeps to enhance the signal-to-noise ratio. As a result, output reports are produced showing defect locations at selected quality control reject-criteria in 0.125 to 0.5 inch thick billet axial cross-sections for the entire billet length. On completion of the cross-sectional analysis the new data for each billet cross-section is supplied into a compatible magnetic tape 43 which may be industry compatible and is maintained for permanent storage and for possible later use.

For any particular setting of the defect gate 32 of the testing system, an output gate signal indicates the presence of a reflection exceeding the setting of the gate. Since a marginally sized defect will not always create a reflection strong enough to trip the gate due to the billet rotation caused variable aspect view of the interrogating transducer over the defect, the output gate signal can vary randomly between "ON" and "OFF" for small defects. The ON/OFF ratio will vary rapidly for defect sizes near the gate setting with larger defects producing the higher ratios. A measurement of this ratio related to a particular location within the billet provides a measurement of the certainty of defect indication at that location. The necessary coordinates for localizing a small volume within a titanium billet are given by the rotation coordinate (theta) and axial translation coordinate (A) of the billet and by the elapsed time between the transmittal of the interrogating pulse and the reception of the reflection echo which is related to the radial position (R). The ratio is evaluated simply by pulsing the given location a fixed number of times and counting the number of output gate signals which are received. For a cross-section through a billet at axial translation A these counts are stored in the computer's core in cells (core locations) related to the R coordinates of the billet. Due to the variation in R produced by the ultrasonic sweep, and the theta scan produced by billet rotation, a matrix of cells in the computer core will be filled with information showing the point-by-point certainty of defect indications in a particular cross-section. By defining a level of certainty of defects, in other words, if N (ON) pulses are received out of a total of M pulses, the cells are tested for count significance and an output is prepared to indicate the results.

Different output devices are provided for the system for displaying the output as for example the graphic display 41 and the printer 42. The graphic display is a very effective form of presentation and provides a conversational capability between the man operating the machine and the testing machine. The alphanumeric-graphic output gives information which will cause the operator to initiate and set inspection criteria and after the inspection the results will be displayed. The inspection results are provided by display of billet cross-sections with an identification of the defective unit cells. The defective unit cells are displayed by graphic symbol "sector-of-annulus-with-point". This symbol represents a defective "sector-of-rectangular torus" unit cell volume of the billet. Typical graphical displays are illustrated in FIGS. 7 and 8 for different A coordinates.

Another output of the system is a high speed line printer 42 and this device prepares permanent documentation concerning the billet inspection. The system is programmed to provide for a choice of two types of printouts, a complete billet defect coordination report as shown below and a billet reject report also shown below.

It is to be realized of course that in the diagnosis of the defect one or more quality control rejection criteria may be applied which relate to the nature, size and shape of significant defects. The necessary scan information is an inherent feature of the computer core images of the billet sections. By analyzing the 1, 2 and 3 distances between cells containing significant data defect counts the computer can evaluate the data with respect to a given quality control rejection criteria and report the location parameters of critical defects as well as specifying which portions of the billet can be accepted and which portions must be rejected. In a specific example perhaps the first 10 inches of the billet are useable then one inch might have to be discarded and the remaining portion of the billet might be satisfactory.

FIG. 6 illustrates various arrangements of the computer for supplying information to an optional Teletype System 54, for example.

It is to be realized that means are provided for automatically changing the angular relationship between the test billet 10 and the transducers 11 and 12 and this might comprise the encoder 27 which could have a mechanical connection to rotate the billet 10. Also the transducers 11 and 12 automatically change their longitudinal position and this might comprise a mechanical connection between the encoder 28 and the transducers so as to move them on the carriage means 31.

A choice of two types of computer printouts can be obtained as illustrated below.

| DEFECT REJECT LENGTH REPORT (RMI-799310B, SCC = 15, R = 2, θ = A = 1) |
| --- |
| ALLOY: T1-4V-6AL    HEAT NO. 8990309 |
| DIAMETER: 16.0 INCHES    LENGTH: 120.0 INCHES |
| OPERATOR: TRW |
| BILLET NO. RMI-799310B |
| LENGTH INCREMENT: 0.250 |
| INSPECTION DATE: 2-APR-74 |
| REPORT DATE: 9-MAY-74 |
| DEFECT CRITERIA: COUNT = 15, R = 2, T = 1, A = 1 |

| REJECTED LENGTH (INCHES) | ACCEPTED LENGTH (INCHES) |
| --- | --- |
|  | 0.00 TO 91.25 |
| 91.25 TO 91.50 |  |
|  | 91.50 TO 120.00 |

END***OF***BILLET
TOTAL ACCEPTED LENGTH = 119.75 INCHES
TOTAL REJECTED LENGTH = 0.25 INCHES
END OF REPORT

| DEFECT COORDINATION REPORT (RMI-799310B, SCC = 15, R = 2, θ = A = 1) |
| --- |
| ALLOY: T1-4V-6AL    HEAT NO: 8990309 |
| DIAMETER: 16.0 INCHES    LENGTH: 120.0 INCHES |
| OPERATOR: TRW |
| BILLET NO. RMI-799310B |
| LENGTH INCREMENT: 0.250 |
| INSPECTION DATE: 2-APR-74 |
| REPORT DATE: 9-MAY-74 |
| DEFECT CRITERIA: COUNT = 15; R = 2, T = 1, A = 1 |

| CROSS-SECTION NUMBER | DEFECT STARTS AT THETA (DEG) | DEFECT STARTS AT RADIUS (INCH) | DEFECT ENDS AT THETA (DEG) | DEFECT ENDS AT RADIUS (INCH) |
| --- | --- | --- | --- | --- |
| 730. | 201.6 | 2.2 | 205.2 | 1.8 |

END**OF**BILLET

Although the invention has been described with respect to preferred embodiments it is not to be so limited as changes and modifications may be made which are within the full intended scope as defined by the appended claims.

I claim as my invention:

1. An ultrasonic inspection system for a test specimen comprising,
a pulser,
a transducer connected to said pulser for transmitting and receiving ultrasonic energy into and from said specimen,
a receiver connected to said transducer, angular indexing means producing an output indicative of the angular position of said transducer relative to said specimen, longitudinal indexing means producing an output indicative of the longitudinal position of said transducer, and a computing and presentation means receiving the outputs of said receiver, said angular indexing means and said longitudinal indexing means and producing an output indicative of the internal structure of said test specimen, wherein said computing and presentation means include a timing means which supplies an input to said pulser, means for changing the angular relationship between said transducer and said test specimen, means for changing the longitudinal relationship between said transducer and said test specimen, an adjustable level gate receiving the output of said receiver and passing echoes above a preset level to said computing and presenting means, and a second transducer mounted adjacent said test specimen on the side opposite said transducer, and an automatic distance amplitude controller receiving the output of said second transducer and supplying an output to said receiver to vary its gain.

2. An ultrasonic inspection system according to claim 1 including a real time presentation means receiving an output of said receiver.

3. An ultrasonic inspection system according to claim 2 where said real time presentation means is an A-scan cathode display.

4. An ultrasonic inspection system according to claim 1 including a display means receiving at least a portion of its input information from storage in said computing and presentation means.

5. An ultrasonic inspection system according to claim 4 wherein said display means comprises a compound B-scan.

6. An ultrasonic inspection system according to claim 4 wherein said display means is an alphanumeric-graphic display.

7. An ultrasonic inspection system according to claim 4 wherein said display means is a printer.

8. An ultrasonic inspection system according to claim 1 wherein said test specimen is cylindrical shaped.

* * * * *